United States Patent [19]

Rainin

[11] 4,242,760
[45] Jan. 6, 1981

[54] INTRAOCULAR LENS STRUCTURE

[76] Inventor: Edgar A. Rainin, 20 Shawn Ct., Danville, Calif. 94526

[21] Appl. No.: 47,319

[22] Filed: Jun. 11, 1979

[51] Int. Cl.³ .......................... A61F 1/16; A61F 1/24
[52] U.S. Cl. .......................................................... 3/13
[58] Field of Search ........................................ 3/13, 1

[56] References Cited

U.S. PATENT DOCUMENTS

| | | | |
|---|---|---|---|
| 3,906,551 | 9/1975 | Otter | 3/13 |
| 3,922,728 | 12/1975 | Krasnov | 3/13 |
| 3,986,214 | 10/1976 | Krasnov | 3/13 |
| 4,085,467 | 4/1978 | Rainin et al. | 3/13 |
| 4,092,743 | 6/1978 | Kelman | 3/13 |
| 4,159,546 | 7/1979 | Shearing | 3/13 |

Primary Examiner—Ronald L. Frinks
Attorney, Agent, or Firm—Bielen and Peterson

[57] ABSTRACT

An intraocular lens structure utilizing a lens which may be placed against the side of the iris and adapted for covering at least a portion of the pupil. The structure includes a first appendage connected to the lens which extends away from the same to the periphery of the iris for engagement. A second appendage connected to the lens includes a first portion which extends away from the lens, a second portion intended for passing through an iris opening and an enlarged end portion which extends to the periphery of the iris and engages the same. The end portions of the first and second appendages are forced against the periphery of the iris.

11 Claims, 9 Drawing Figures

# INTRAOCULAR LENS STRUCTURE

BACKGROUND OF THE INVENTION

The present invention relates to an intraocular lens structure or pseudophakos designed to be placed in either the anterior or posterior chamber of the eye after the removal of a natural lens as a result of a cataract condition.

It has been found that the insertion of an intraocular lens is by far the best solution to correcting vision after cataract surgery. The proper placement of an intraocular lens always involves the risk of damage to the eye during the insertion process as well as at a later time period if the intraocular lens dislocates.

Prior intraocular lens structures have employed the use of the iris to fix the same. In this regard references made to U.S. Pat. No. 3,906,551 issued to Otter, U.S. Pat. No. 3,922,728 issued to Krasnof, U.S. Pat. No. 4,085,467 issued to Rainin et al as examples of this system of fixation. Although this type of lens structure has been quite successful it is generally believed that proper insertion requires greater than average skill on the part of the eye surgeon performing this work.

Recently there have been a family of intraocular lenses which are simply wedged between opposite sides of the eye chamber in the vicinity of the iris. Such lenses were an off-shoot of an early development by Strampelli, who devised such a lens in 1953. Generally this type of lens must be perfectly sized to avoid dislocation and a reentry to the eye by the surgeon for relocation of the lens or insertion of a new lens. It has been found that the wedging type intraocular lens may be placed in the anterior chamber of the eye and fixed by the anterior chamber angle. Likewise, this lens may be placed in the posterior chamber and held in place at the ciliary sulcus. Early designs of wedging type lenses include the Barraquer lens which includes at least one springy leg. The resilience of this leg offers a degree of adjustment and greatly reduces the possibility of dislocation during the postoperative time period. Although originally designed for positioning within the anterior chamber, recent modifications to the Barraquer lens, eg: the Shearing lens, permit posterior chamber fixation as well. At least one design of the Shearing lens employs a pair of springy legs attached to the lens. One resilient leg of the Shearing lens is placed through a chemically dilated pupil to the area of the ciliary sulcus. The second resilient leg is coiled and forced through the pupil with the lens to the posterior chamber. The second resilient leg is released and directed toward the ciliary sulcus at a position therein opposite to that of the first resilient leg. The Shearing lens may be used with extra capsular surgery only since a secondary support, by the remaining portion of the natural lens, is necessary if good fixation at the ciliary sulcus is not achieved. In addition, insertion of the Shearing lens may result in severence of the zonule which would allow the Shearing lens to travel into the vitreous humor behind the iris. Along these lines, maximum pupil size is desirable to insure proper fixation. Adequate dilation of the pupil is not possible in every case. Moreover, the releasing of the second resilient leg creates a whip-like action which can tear the iris resulting in bleeding and damage to the eye. All in all, posterior fixation of the Shearing lenses is difficult to predict.

There is a need for a wedging type lens which may be easily fixed into the posterior or anterior chamber of the eye which offers a secondary means of support, without substantial damage to the eye during and after insertion.

SUMMARY OF THE INVENTION

In accordance with the present invention a novel intraocular lens structure is provided.

The structure includes a lens or optical zone portion intended for placement against the side of the iris and adapted for covering at least a portion of the pupil. The lens would be sized for the proper optical correction necessary to correct aphakia resulting from cataract removal. The structure further includes a first appendage which is connected to the lens and extends away from the same to the periphery of the iris. The first appendage includes means for urging engagement of the same in the vicinity of the periphery of the iris. For example, in the anterior chamber of the eye the first appendage may engage the anterior chamber angle found between the iris and cornea. Likewise, the first appendage may engage ciliary sulcus, a notch in the ciliary body, when used in the posterior chamber.

The present invention also includes as one of its elements a second appendage which provides a secondary means of support for the lens. The second appendage is connected to the lens and has a first portion extending therefrom, a second portion connected to the first portion intended for passing through the iris opening, and an enlarged end portion intended for extending to the periphery of the iris. The second appendage engages the periphery of the iris in the same manner described in the first appendage hereinabove. Again, the second appendage includes means for urging engagement of the same with the periphery of the iris.

The means for urging engagement of the first and second appendages to the periphery of the iris may take the form of a spring mechanism and the like. It has been found that simply forming at least a portion of the first and second appendages of resilient material produces a spring-like effect. In addition, each appendage may be an elongated member having a curved end portion with a blunted tip or cap to prevent damage to the eye tissue during and after insertion of the lens structure.

The present invention may also be deemed to include a method of inserting an intraocular lens structure which includes an optical zone, and first and second appendages extending therefrom. The method would include placing the optical zone adjacent the iris such that the optical zone covers at least a portion of the pupil. The first appendage is directed toward the periphery of the iris and caused to engage the same. The second appendage is directed through an opening in the iris and then directed toward the periphery of the iris resulting in engagement of the second appendage with the periphery of the iris. In addition, the method may further include the step of maintaining the engagement of the first and second appendages with the periphery of the iris.

It should be apparent that a new and useful intraocular lens structure has been described which is novel and useful for the purposes described herein.

It is therefore an object of the present invention to provide an intraocular lens structure which may be employed to correct aphakia after cataract surgery accomplished by extra capsular cataract extraction or intracapsular cataract extraction.

It is another object of the present invention to provide an intraocular lens structure which may be easily inserted into the posterior chamber of the eye without penetrating the vitreous cavity and the surface of the retina.

It is yet another object of the present invention to provide an intraocular lens structure which may be inserted without the necessity of chemical dilation of the pupil.

It is a further object of the present invention to provide an intraocular lens structure which may be easily inserted into the anterior or posterior chamber of the eye without tearing the iris tissue.

It is still another object of the present invention to provide an intraocular lens structure which provides primary and secondary means of support of the optical zone.

It is another object of the present invention to provide an intraocular lens structure and method for inserting the same when the user is able to visually guide at least one means of fixation of the optical zone and to stabilize the lens structure during insertion thereof in either the anterior or posterior chamber of the eye.

The invention possesses other objects and advantages especially as concerns particular features and characteristics thereof which will become apparent as the specification continues.

Various aspects of the present invention will evolve from the following detailed description of the preferred embodiments thereof which should be taken in conjunction with the accompanying drawings.

Figure 1:
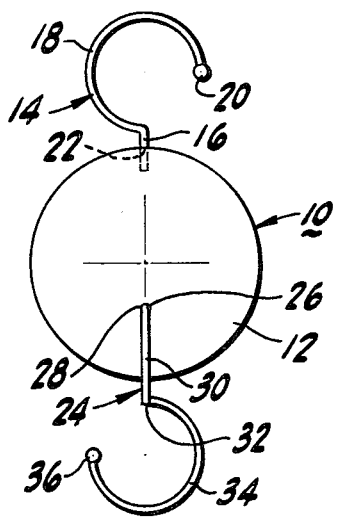
FIG. 1 is a top plan view of an embodiment of the present invention intended for fixation in the posterior chamber of the eye.

For a better understanding of the invention reference is made to the following detailed description.

DESCRIPTION OF THE PREFERRED EMBODIMENTS

With reference to the drawings the invention as a whole is depicted on the figures illustrated thereupon and denoted by reference character 10. The intraocular lens structure 10 includes as one of its elements a lens portion for optical zone 12, FIG. 1. The lens portion 12 may be constructed of any biologically inert and transparent material suitable for optical correction such as methylmethacrylate, quartz, ophthalmic glass, and other materials known in the art. Lens 12 may or may not include a haptic; the embodiments shown do not show a haptic for the sake of simplicity.

First appendage 14 fixes to lens portion 12 and extends away from the same. First appendage 14 may be molded integrally with lens portion 12 or connected by an adhesive, ultrasonic welding, fusion, or any other connection method known in the art. As may be seen from FIG. 1, first appendage 14 is an elongated member having a relatively straight portion 16 and a curved terminus 18. In other words, straight portion 16 connects to lens portion 12 at the proximal end and to curved portion 18 at the distal end thereof. A knob 20 is fixed to the terminal portion 18 to prevent damage to human tissue within the eye. It should be noted that first appendage 14 is constructed of biologically inert and nonabsorbative material such as methylmethacrylate, polypropylene, platinum, and the like. First appendage 14 is connected to lens portion 12 and opening 22. The present embodiment anticipates that first appendage 14 is resilient or springy such that it will return to the position shown on FIG. 1 after compression or extension away from the illustrated configuration.

Lens structure 10 embraces a second appendage 24 as a necessary element thereof. Second appendage 24 may be constructed of materials similar to that used in the construction of first appendage 14. Second appendage 24 includes a first portion 26 which connects to lens portion 12 at point 28. Second appendage 24 may also have a straight section 30. Second portion 32 of second appendage 24, whose function will be hereinafter described, links first portion 26 with enlarged end portion 34, which is shown as having a curved configuration. A knob 36 caps the terminus of end portion 34 and functions exactly as knob 20 functions. Second appendage 24 may be fairly rigid or springy in a manner similar to first appendage 14.

Figure 2:
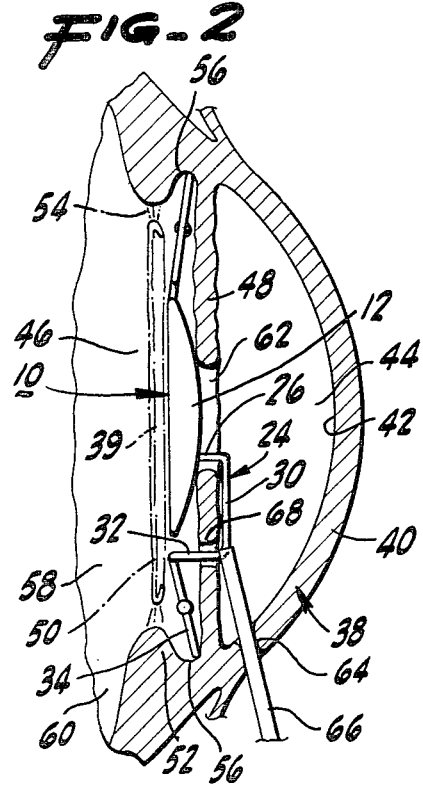
FIG. 2 is a sectional view of the intraocular lens structure of FIG. 1 fixed within an eye.
Figure 7:
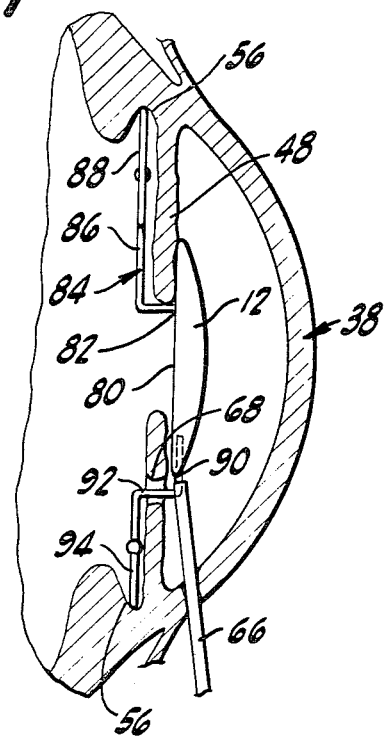
FIG. 7 is a sectional view depicting the lens structure shown in FIG. 6 fixed within an eye.

Lens structure 10 is intended for insertion and fixation within an eye 38, FIGS. 2 and 7, after cataract removal either by intracapsular or extra capsular surgical procedures. Eye 38 includes a cornea 40 having an endothelial layer 42. Anterior chamber 44 and posterior chamber 46 are defined by the position of iris 48. The natural lens 50 is depicted in FIG. 7 as having been removed. FIG. 2 shows eye 38 after an extra capsular surgical procedure whereby a relatively flattened membrane 39 remains (phantom). Lens structure 10 is usable after extra capsular or intracapsular surgery. Natural lens 50 is normally connected to the ciliary body 52 by a plurality of zonules 54 (shown in phantom). Wedging type intraocular lenses have found very good primary support in the ciliary sulcus 56 of the posterior chamber 46, FIG. 2. Vitreous humor 58 fills a vitreous cavity 60 usually found behind natural lens 50.

As shown in FIG. 2, lens structure 10 may be placed in posterior chamber 46 through pupil 62, which may be mechanically dilated. Initially lens structure 10 is slipped through an opening 64 of cornea 40 below the end of endothelial layer 42 which aligns with pupil 62. A pair of tweezers 66 is employed to stabilize and to steer optical zone and first appendage 14 through pupil 62. At this point there is a distinct danger that first appendage 14 may sever zonules 54 in the inferior zone of the posterior chamber 46. However, second appendage 24 offers a firm grip which prevents lens structure 10 from traveling into the vitreous cavity 60 and possibly to the retinal area therebehind (not shown). Curved portion 18 of first appendage 14 fits within ciliary sulcus 56 at the periphery of iris 48 serving as a means for primary support of optical zone 12.

Iris opening 68 may be cut by the surgeon through the superior portion of iris 48. Second appendage 24 passes through iris opening 68 such that enlarged end portion 34 slips through iris opening 66 similarly to a button being pushed through a button hole. The surgeon may view enlarged portion 34 through iris opening 68 to insure that enlarged portion 34 faithfully enters ciliary sulcus 56 as another means of primary support for optical zone 12. Also, second appendage 24 when positioned offers a positive means of secondary support for lens portion 12 of lens structure 10, since second portion 32 of second appendage 24 will bear on the side of iris opening 68 and enlarged end portion 34 of second appendage 24 will resist passage through iris opening 68. Thus, inferior dislocation of first appendage 14 and/or end portion 34 of second appendage 24 will be attenuated by the secondary support offered by second appendage 24. It should be noted that tertiary support for optical zone 12 may derive from membrane 39, FIG. 2.

Figure 3:
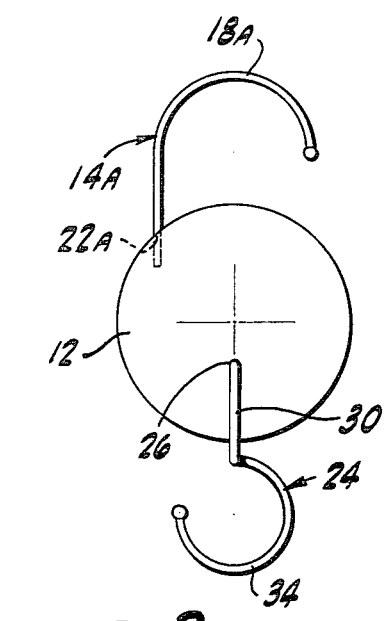
FIG. 3 is a top plan view of another embodiment of the present invention intended for fixation in the posterior chamber of an eye.

FIG. 3 depicts another embodiment of the present invention wherein first appendage 14A includes a curved terminus 18A. The connection opening 22A is offset from relatively straight section 30 of second appendage 24. The embodiment described in FIG. 1 depicts straight portion 16 of first appendage 14 and straight portion 30 of second appendage 24 as being coplanar.

Figure 4:
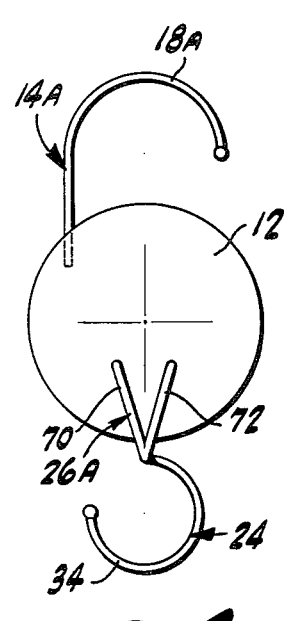
FIG. 4 is a top plan view of another embodiment of the present invention intended for fixation in the posterior chamber of an eye.

FIG. 4 shows yet another embodiment of the posterior chamber lens structure 10 which includes a second appendange 24 having a first portion 26A which is split into a pair of legs 70 and 72.

Figure 5:
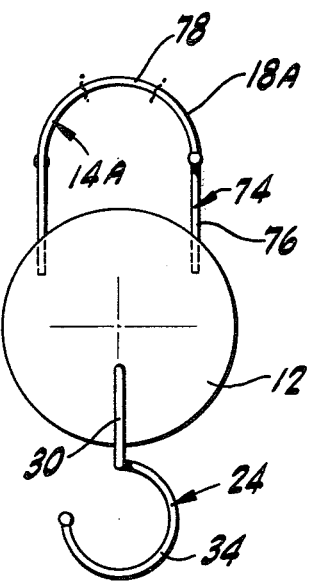
FIG. 5 is a top plan view of another embodiment of the present invention intended for fixation in the posterior chamber of an eye.

FIG. 5 describes another variation of lens structure 10 where first appendage 14A is joined by a third appendage 74 having a straight portion 76 and a curved terminus 78.

Figure 6:
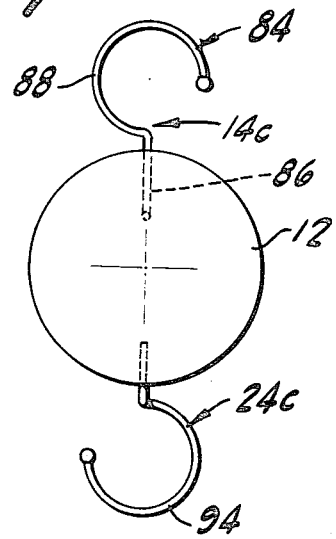
FIG. 6 is a top plan view of another embodiment of the present invention intended for fixation in the anterior chamber of an eye.
Figure 8:
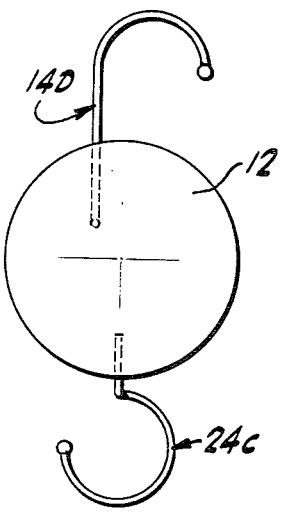
FIG. 8 is a top plan view of another embodiment of the present invention intended for placement in the anterior chamber of the eye.
Figure 9:
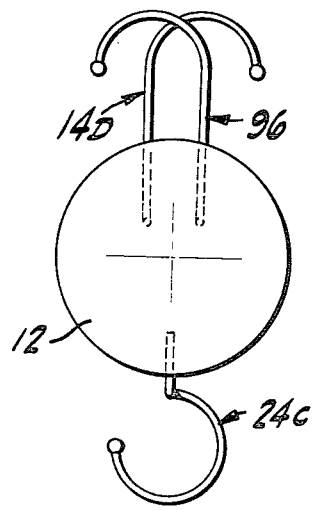
FIG. 9 is a top plan view of another embodiment of the present invention intended for placement in the anterior chamber of an eye.

Turning to FIG. 6, another embodiment of the present invention is illustrated where lens portion 12 includes a first appendage 14C and a second appendage 24C. First appendage 14C extends from the lower surface 80 of optical zone 12 at point 82 thereon. Leg 14C includes a first portion 84 having an elongated straight section 86 and a curved terminus 88. Second appendage 24C includes a first portion 90 which offers a gripping support for tweezers 66, FIG. 7, a second portion 92 which passes through the iris opening 68, and an enlarged end portion 94. As shown by FIG. 7, curved terminus 88 and enlarged end portion 94 wedge into the ciliary sulcus 56 of eye 38. FIG. 8 depicts another embodiment of the anterior chamber version of the present invention where first appendage 14D connects off center in relation to optical zone 12. Likewise, appendage 14D may be joined by a third appendage 96 similar in structure but oriented oppositely in relation to appendage 14D, FIG. 9. In operation, the surgeon may insert the embodiments of the present invention depicted in FIGS. 1 through 5 as heretofore described. The anterior chamber version shown in FIGS. 6 through 9 is similarly fixed except that lens portion 12 is kept to the anterior chamber side of iris 48.

While in the foregoing specification embodiments of the present invention have been set forth in considerable detail for the purposes of making a complete disclosure of the invention, it will be apparent to those of ordinary skill in the art that numerous changes may be made in such details without departing from the spirit and principles of the invention.

What is claimed is:

1. An intraocular lens structure intended for insertion within the eye; the iris of the eye having an opening therethrough comprising:
    a. lens intended for placement adjacent a side of the iris, said lens adapted for covering at least a portion of the pupil;
    b. first appendage being connected to said lens and intended for extending away from said lens to the periphery of the iris for engagement therewith;
    c. second appendage being connected to said lens having a first portion extending from said lens, a second portion intended for passing through the iris opening and an enlarged end portion intended for extending to the periphery of the iris for engagement therewith;
    d. means for urging engagement of said first appendage to the periphery of the iris;
    e. means for urging engagement of said second appendage to the periphery of the iris.

2. The intraocular lens structure of claim 1 in which said means for urging engagement of said first appendage to the periphery of the iris comprises forming at least a portion of said first appendage of resilient material.

3. The intraocular lens structure of claim 2 in which said first appendage is an elongated member having a curved portion intended for engagement with the periphery of the iris.

4. The intraocular lens structure of claim 3 in which said means for urging engagement of said second appendage to the periphery of the iris comprises forming at least a portion of said second appendage of resilient material.

5. The intraocular lens structure of claim 4 in which said enlarged end portion of said second appendage intended for extending to the periphery of the iris for engagement therewith comprises an elongated member having a curved portion intended for engagement with the periphery of the iris.

6. The intraocular lens structure of claim 5 in which said enlarged end portion of said second appendage has a dimension larger than the iris opening.

7. The intraocular lens structure of claim 6 in which said first appendage further includes a relatively straight portion connected to said lens at the proximal end and connected to said curved portion at the distal end, and said first portion of said second appendage includes a straight portion, said straight portion of said first and second appendages being coplanar.

8. The intraocular lens structure of claim 6 which further comprises a third appendage connected to said lens and intended for extending away from said lens to the periphery of the iris for engagement therewith, and means for urging engagement of said third appendage to the periphery of the iris.

9. A method of inserting an intraocular lens including first and second appendages extending from an optical zone comprising the steps of:
    a. placing the optical zone adjacent the iris such that said optical zone covers at least a portion of the pupil;
    b. directing the first appendage toward the periphery of the iris and causing engagement of said first appendage with said periphery;

c. directing the second appendage through an opening in the iris and then directed toward the periphery of the iris and causing engagement of said second appendage with said periphery.

10. The method of claim 9 which additionally comprises the step of maintaining said engagement of said first and second appendages with the periphery of the iris.

11. The method of claim 9 which additionally comprises the step of stabilizing said intraocular lens structure by gripping said second appendage before said step of placing the optical zone adjacent the iris.

* * * * *